United States Patent [19]

van Andel

[11] Patent Number: Plant 5,501

[45] Date of Patent: Jun. 25, 1985

[54] ALSTROEMERIA NAMED STALROBU

[75] Inventor: Jacob van Andel, Aalsmeer, Netherlands

[73] Assignees: B. V. Handelskwekerij; M. C. van Staaveren, both of Aalsmeer, Netherlands

[21] Appl. No.: 522,314

[22] Filed: Aug. 11, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new and distinct alstroemeria cultivar particularly distinguished by the generally light red-purple coloration of its very large flowers, the petals of which have a rhodamine purple body color overcase by a longitudinally extending central portion of a darker roseine purple color which presents a very unusual variegated color display. This new plant is further distinguished by its continuous and profuse blooming habit, its vigorous, strong and upright growth and by the excellent lasting quality of its blooms both on the plant and as cut flowers.

1 Drawing Figure

BACKGROUND OF THE INVENTION

This new alstroemeria cultivar originated as a seedling resulting from my crossing of selected and individually identified plants maintained in greenhouse at Aalsmeer, Holland, for breeding and developmental purposes. This particular seedling was selected by me because of the very attractive red-purple coloration of its blooms, its profuse production of blooms and its apparent very fast and vigorous growth habit and I reproduced this plant at Aalsmeer through root division with very favorable results. Subsequently I carried that propagation through several generations, thereby determining that the novel characteristics of coloration and growth habit of this new plant would remain true from generation to generation and appeared to be firmly fixed.

DESCRIPTION OF THE DRAWING

My new alstroemeria cultivar is illustrated by the accompanying full color photographic drawing which shows a full umbel of the inflorescence with buds and flowers in various stages of opening, the color rendition being as nearly true to those specified as is reasonably possible to obtain by conventional photographic procedures.

DESCRIPTION OF THE NEW PLANT

The following is a detailed description of my new alstroemeria cultivar with the color designations being according to The R.H.S. Colour Chart of The Royal Horticultural Society of London, England.

THE PLANT

Origin: Seedling.

Parentage:

*Seed parent.*—Stock Variety No. 2171-1.

*Pollen parent.*—Stock Variety No. 3126-1. Note: These varieties are identified by permanent business records maintained at Aalsmeer, Holland.

Classification: Alstroemeria Hybrid.

Form: Erect bush.

Height:

*Main stem or cane.*—About 170 cm.

Growth: Vigorous, strong and upright.

Root stock: Tuberous. The tubers bear many buds during the year, from which flower stalks grow in various stages of development during the course of the year.

Branching: Each flower stalk branches at its top to form an umbel having about eight or nine flower bearing stems.

Foliage:

*Quantity.*—Abundant with about thirty to forty leaves per stem.

*Shape of leaf.*—Elliptic.

*Size of leaf.*—Various, depending upon season.

*Texture.*—Leathery.

*Color.*—Upper side — Dark Green. Under side — Grey Green.

THE BUD

Form: Pear-shaped.

Size: Medium.

*Diameter.*—1.5 cm.

*Length.*—About 3.5 cm.

Opening rate: Normal.

Calyx: This bud has no calyx and the six petals of the flower are a perianth.

Peduncle:

*Length.*—About 2 cm. borne on an umbel stem of about 12 to 18 cm. in length.

THE FLOWER

Blooming habit: Continuous during early Spring and early Fall seasons with profuse production of very large flowers.

Flower size: Very large.

*Diameter.*—About 6 to 6.5 cm.

*Depth.*—About 6 cm.

Shape: Generally funnel-like.

Borne: Singly.

Petalage:

*Number of petals.*—Six.

*Arrangement.*—Two concentric circles of three petals each.

*Form.*—Broad ovate.

*Texture.*—Soft.

*Appearance.*—Shiny.

*Color.*—Outer Petals: Body — 68D with center portion broadly streaked or blotched with 68A. Reverse side — 68C with inner center portion of 68A. Inside Petals: Body — 68C with inner center portion of 68A.

Main stem or cane:

*Length.*—About 170 cm.

*Color.*—Middle Green.

*Character.*—Strong and upright.

Lasting quality of flowers:

*On the plant.*—15 to 20 days.

*As cut flowers.*—10 to 15 days.

REPRODUCTIVE ORGANS

Stamens:

*Number.*—Six, one opposite each petal.

*Anthers.*—Length — About 8 mm. Color: Brown-Purple-Grey.

*Filaments.*—Length — About 4 cm. Color: Pink.

*Pollen.*—Color — Grey Purple.

Pistils:

*Number.*—One.

Style.—Length — About 7 mm.

*Color.*—Pink.

*Stigma.*—Color — Pink.

This alstroemeria cultivar is particularly distinguished by its very large and numerous flowers with variegated light red-purple coloration and by its profuse production of flowers on relatively long, strong, umbel stems.

I claim:

1. The new and distinct variety of alstroemeria plant, substantially as herein shown and described, characterized by the distinctive red-purple coloration of its large flowers carried by sturdy, long and generally straight umbel stems.

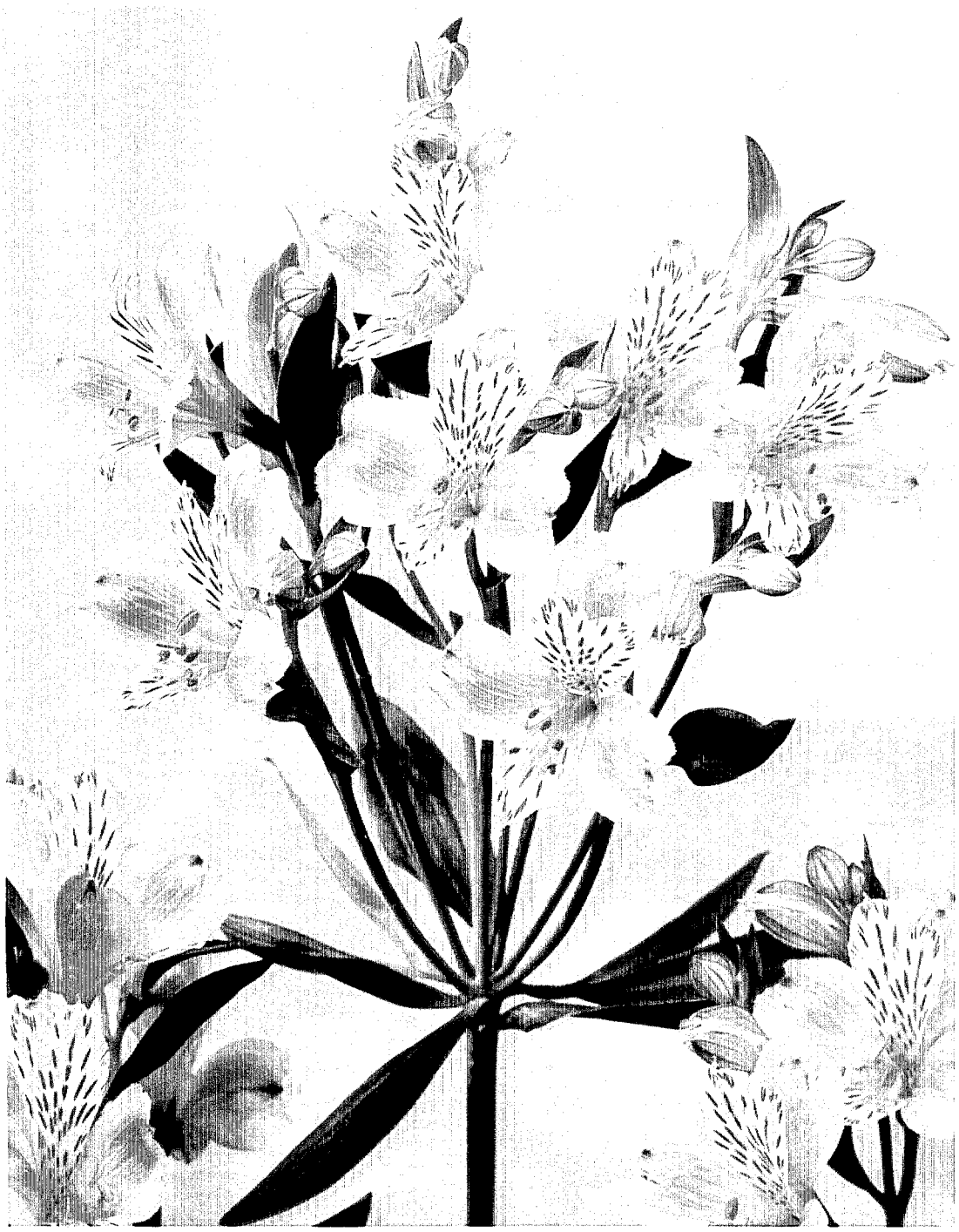

* * * * *